(12) United States Patent
Park et al.

(10) Patent No.: US 12,383,234 B2
(45) Date of Patent: Aug. 12, 2025

(54) ULTRASONIC IMAGING APPARATUS AND METHOD FOR CONTROLLING THE SAME

(71) Applicant: SAMSUNG MEDISON CO., LTD., Gangwon-do (KR)

(72) Inventors: Ji Young Park, Hwaseong-si (KR); Ki Wan Choi, Anyang-si (KR); Seong Hyeon Choi, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 246 days.

(21) Appl. No.: 17/430,563

(22) PCT Filed: Jul. 25, 2019

(86) PCT No.: PCT/KR2019/009210
§ 371 (c)(1),
(2) Date: Aug. 12, 2021

(87) PCT Pub. No.: WO2020/184790
PCT Pub. Date: Sep. 17, 2020

(65) Prior Publication Data
US 2022/0125412 A1    Apr. 28, 2022

(30) Foreign Application Priority Data
Mar. 14, 2019  (KR) .......................... 10-2019-0029265

(51) Int. Cl.
*A61B 8/00*  (2006.01)
*A61B 8/06*  (2006.01)
(52) U.S. Cl.
CPC ................ *A61B 8/485* (2013.01); *A61B 8/06* (2013.01); *A61B 8/4477* (2013.01); *A61B 8/5207* (2013.01); *A61B 8/54* (2013.01)

(58) Field of Classification Search
CPC ......... A61B 34/10; A61B 34/20; A61B 34/25; A61B 90/37; A61B 2034/102;
(Continued)

(56) References Cited

U.S. PATENT DOCUMENTS 8,852,102 B2   10/2014  Miyachi
9,072,493 B1   7/2015   Yoshikawa
(Continued)

FOREIGN PATENT DOCUMENTS

AU    2016200737 B2 * 10/2017 ............ A61M 25/00
CN    106233333 A   * 12/2016 ............ G06T 19/00
(Continued)

OTHER PUBLICATIONS

Cinthio et. al.,Longitudinal movements and resulting shear strain of the arterial wall Feb. 10, 2006 (Year: 2006).*
(Continued)

*Primary Examiner* — Sean D Mattson
(74) *Attorney, Agent, or Firm* — Morgan Lewis & Bockius LLP

(57) ABSTRACT

Provided is an ultrasonic imaging apparatus capable of obtaining a more accurate shear wave elastic image by removing inefficient areas such as blood vessels using a shear wave observation signal in a section where an object is not affected by a push pulse, and a method for controlling the same. The ultrasonic imaging apparatus according to an embodiment includes: an ultrasonic probe configured to irradiate a push pulse, irradiate a first observation signal to the object after the push pulse is irradiated, and irradiate a second observation signal to the object; a controller configured to determine an inefficiency region of the object, and generate a shear wave elastic image based on the determined
(Continued)

inefficiency region for each region of the object; and a display configured to display the generated shear wave elastic image.

10 Claims, 15 Drawing Sheets

(58) Field of Classification Search
CPC ...... A61B 2034/105; A61B 2034/2065; A61B 2090/365; A61B 2090/376; A61B 2017/00207; A61B 90/36; A61B 2034/2048; A61B 2090/3612; A61B 2090/372; A61B 2090/3762; A61B 2090/502; G06N 3/045; G06N 3/08
See application file for complete search history.

(56) References Cited

U.S. PATENT DOCUMENTS

| | | | |
|---|---|---|---|
| 11,504,087 B2 * | 11/2022 | Kong | A61B 8/42 |
| 2013/0317361 A1 | 11/2013 | Tabaru et al. | |
| 2016/0350503 A1 * | 12/2016 | Jun | A61B 8/465 |
| 2016/0367223 A1 | 12/2016 | Honjo et al. | |
| 2017/0112471 A1 * | 4/2017 | Toji | A61B 8/4254 |
| 2020/0060653 A1 | 2/2020 | Kong et al. | |

FOREIGN PATENT DOCUMENTS

| | | |
|---|---|---|
| EP | 2964099 | 1/2016 |
| JP | 2012-100997 A | 5/2012 |
| JP | 2012-183261 A | 9/2012 |
| JP | 2013-244162 A | 12/2013 |
| JP | 5501999 B2 | 5/2014 |
| JP | 2015-058193 A | 3/2015 |
| JP | 2015-126955 A | 7/2015 |
| JP | 2017-079977 A | 5/2017 |
| JP | 6230891 B2 | 11/2017 |
| KR | 10-2018-0054360 A | 5/2018 |
| KR | 10-2018-0109500 A | 10/2018 |
| KR | 10-1931748 B1 | 3/2019 |
| WO | 2012/105152 A1 | 8/2012 |
| WO | 2014/136018 A1 | 9/2014 |
| WO | WO-2017091013 A1 * 6/2017 ............... A61N 7/00 |

OTHER PUBLICATIONS

Extended European Search Report dated Feb. 11, 2022 issued in European Patent Application No. 19918564.6.
International Search Report dated Dec. 11, 2019 issued in International Patent Application No. KR2019/009210 (with English translation).
Office Action issued Feb. 14, 2024 for European Patent Application No. 19918564.6.
Office Action issued Feb. 19, 2024 for Korean Patent Application No. 10-2019-0029265 (See English Translation).
Notice of Allowance dated Oct. 10, 2024, issued in corresponding Korean Patent Application No. 10-2019-0029265 with an English translation.

* cited by examiner (a)

(b)

(a)

(b)

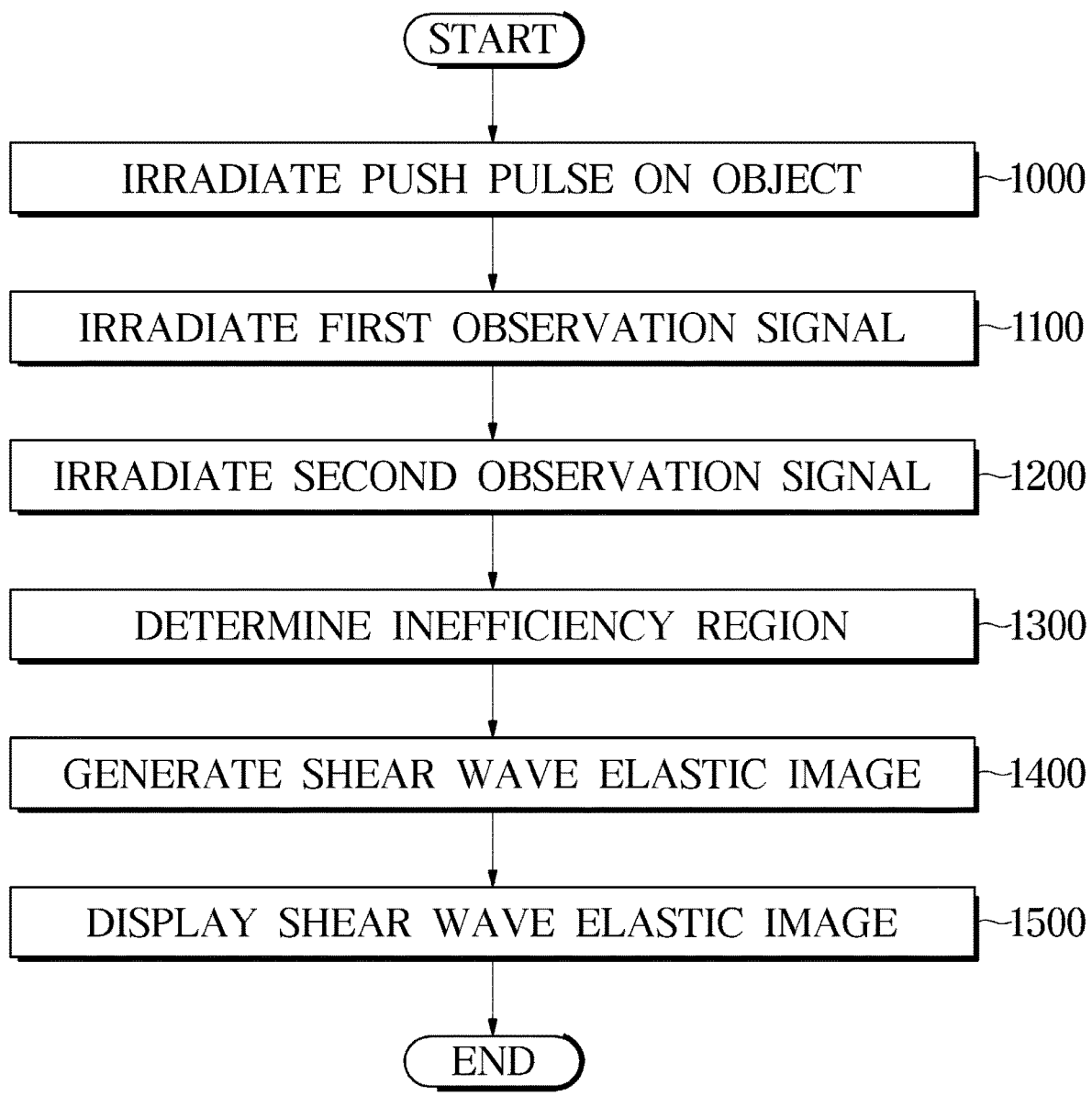

ULTRASONIC IMAGING APPARATUS AND METHOD FOR CONTROLLING THE SAME

CROSS-REFERENCE OF RELATED APPLICATIONS

This application is the U.S. National Phase under 35 U.S.C. § 371 of International Patent Application No. PCT/KR2019/009210, filed on Jul. 25, 2019, which in turn claims the benefit of Korean Application No. 10-2019-0029265, filed on Mar. 14, 2019, the entire disclosures of which applications are incorporated by reference herein.

TECHNICAL FIELD

The present disclosure relates to an ultrasonic imaging apparatus for obtaining an image inside an object using ultrasound and a method for controlling the same.

BACKGROUND ART

The ultrasonic imaging apparatus irradiates an ultrasonic signal generated from a transducer of a probe to an object, and receives information of an echo signal reflected from the object to obtain an image of a region inside the object.

The ultrasonic imaging apparatus is widely used in the medical diagnosis field because the ultrasonic imaging apparatus has no radiation exposure, has higher stability than an X-ray imaging device, may display images in real time, and is inexpensive and portable compared to a magnetic resonance imaging device.

Unlike normal tissue, when factors such as cancer or cirrhosis occur and the tissue strength changes, the ultrasonic imaging apparatus may generate a shear wave in tissue using a push pulse, may diagnose factors such as cancer or liver cirrhosis more accurately by calculating the elastic value of the shear wave using the change in tissue displacement caused by the shear wave. However, a region such as a blood vessel in which displacement change occurs by itself or a bone in which displacement change does not occur due to high strength exists inside the body, and in such region, an accurate shear wave elastic value may not be calculated. Also, a problem in that the shear wave elastic value of the region of interest in the object is inaccurately calculated due to movement of the body, such as shaking of the probe, movement of blood vessels, respiration, and heartbeat, may be occurred. In order to solve such a problem, an ultrasonic imaging apparatus that calculates an accurate shear wave elastic value by calculating the displacement of an object tissue using a push pulse is required.

DISCLOSURE

Technical Problem

An ultrasonic imaging apparatus capable of obtaining a more accurate shear wave elastic image by removing inefficient areas such as blood vessels using a shear wave observation signal in a section where an object is not affected by a push pulse, and a method for controlling the same are provided.

Technical Solution

An aspect of the present disclosure provides a ultrasonic imaging apparatus comprising an ultrasonic probe configured to irradiate a push pulse to generate a shear wave to an object, irradiate a first observation signal to the object after the push pulse is irradiated, and irradiate a second observation signal to the object before the push pulse is irradiated or after the first observation signal is irradiated; a controller configured to determine an inefficiency region of the object based on displacement data for each region of the object obtained from the irradiated second observation signal, and generate a shear wave elastic image based on the determined inefficiency region and displacement data for each region of the object obtained from the irradiated first observation signal; and a display configured to display the generated shear wave elastic image.

The first observation signal and the second observation signal may include a plurality of ultrasound signals having a predetermined time interval, and a time interval of each of the plurality of ultrasound signals included in the second observation signal may be longer than or equal to a time interval of each of the plurality of ultrasound signals included in the first observation signal.

The second observation signal may be irradiated for a shorter or equal time than the first observation signal.

The time interval of each of the plurality of ultrasound signals included in the second observation signal may be less than or equal to 500 microsecond.

The second observation signal may be irradiated for more than 10 millisecond.

The inefficiency region may include at least one of a blood vessel region in which blood flow exists and a region in which tissue movement occurs.

The controller may determine a region in which a displacement value or a shear wave velocity value is greater than or equal to a predetermined value among regions of the object, and determine the determined region as an inefficiency region, based on the displacement data for each area of the object obtained from the irradiated second observation signal.

The controller may determine a shear wave elastic value for each area of the object based on the displacement data for each area of the object obtained from the irradiated first observation signal, generate a shear wave elastic image of the object based on the determined shear wave elastic value for each region, and generate a shear wave elastic image so that the shear wave elastic value of the determined inefficiency region is not displayed.

The controller may determine a shear wave elastic value for each area of the object based on the displacement data for each area of the object obtained from the irradiated first observation signal, generate a shear wave elastic image of the object based on the determined shear wave elastic value for each region, and generate a shear wave elastic image by changing a reliability measurement index (RMI) of the shear wave elastic value of the determined inefficiency region.

The controller may control the display to display a shear wave elastic image in which the determined shear wave elastic value of the inefficient region is not displayed.

The controller may control the display to display a shear wave elastic image to which the changed reliability measurement index (RMI) is applied.

The controller may control the display to indicate the changed reliability measurement index (RMI).

The controller may control the display to display the determined inefficiency area.

Another aspect of the present disclosure provides a method for controlling ultrasonic imaging apparatus, comprising irradiating an object with a second observation signal; irradiating a push pulse for generating a shear wave to the object after the second observation signal is irradiated to the object; irradiating a first observation signal to the object after the push pulse is irradiated; determining an inefficiency region of the object based on displacement data for each region of the object obtained from the irradiated second observation signal; generating a shear wave elastic image based on the displacement data for each region of the object obtained from the irradiated first observation signal and the determined inefficiency region; and displaying the generated shear wave elastic image.

The first observation signal and the second observation signal may include a plurality of ultrasound signals having a predetermined time interval, and a time interval of each of the plurality of ultrasound signals included in the second observation signal may be longer than or equal to a time interval of each of the plurality of ultrasound signals included in the first observation signal.

The second observation signal may be irradiated for a shorter or equal time than the first observation signal.

The time interval of each of the plurality of ultrasound signals included in the second observation signal may be less than or equal to 500 microsecond.

The second observation signal may be irradiated for more than 10 millisecond.

The inefficiency region may include at least one of a blood vessel region in which blood flow exists and a region in which tissue movement occurs.

The determining of an inefficiency region of the object based on displacement data for each region of the object obtained from the irradiated second observation signal may include determining a region in which a displacement value or a shear wave velocity value is greater than or equal to a predetermined value among regions of the object, and determining the determined region as an inefficiency region based on the displacement data for each area of the object obtained from the irradiated second observation signal.

The generating a shear wave elastic image based on the displacement data for each region of the object obtained from the irradiated first observation signal and the determined inefficiency region, may include determining a shear wave elastic value for each area of the object based on the displacement data for each area of the object obtained from the irradiated first observation signal; and generating a shear wave elastic image based on the determined shear wave elastic value for each region and generating the shear wave elastic image so that the determined shear wave elastic value of the inefficient region is not displayed.

The generating a shear wave elastic image based on the displacement data for each region of the object obtained from the irradiated first observation signal and the determined inefficiency region, may include determining a shear wave elastic value for each area of the object based on the displacement data for each area of the object obtained from the irradiated first observation signal; generating the shear wave elastic image based on the determined shear wave elastic value for each region; and generating a shear wave elastic image by changing a reliability measurement index (RMI) of the shear wave elastic value of the determined inefficiency region.

The method for controlling ultrasonic imaging apparatus according to an embodiment, may further include displaying a shear wave elastic image in which the shear wave elastic value of the determined inefficiency region is not displayed.

The method for controlling ultrasonic imaging apparatus according to an embodiment, may further include displaying the changed reliability measurement index (RMI).

The method for controlling ultrasonic imaging apparatus according to an embodiment, may further include displaying the determined inefficiency area.

The method for controlling ultrasonic imaging apparatus according to an embodiment, the method may include irradiating a push pulse to the object to generate a shear wave to an object; irradiating a first observation signal to the object after the push pulse is irradiated; irradiating a second observation signal to the object after the first observation signal is irradiated; determining an inefficiency region of the object based on displacement data for each region of the object obtained from the irradiated second observation signal; generating a shear wave elastic image based on the displacement data for each region of the object obtained from the irradiated first observation signal and the determined inefficiency region; and displaying the generated shear wave elastic image.

Advantageous Effects

According to the ultrasonic imaging apparatus and its control method according to one aspect, since it is possible to calculate a more accurate shear wave elastic value by removing the inaccurate measurement area such as blood vessels using the shear wave observation signal in the section where the object is not affected by the push pulse, a highly reliable shear wave elastic image can be provided to the user.

DESCRIPTION OF DRAWINGS

These and/or other aspects of the invention will become apparent and more readily appreciated from the following description of the embodiments, taken in conjunction with the accompanying drawings of which:

FIG. 11 is a control flowchart of an ultrasonic imaging apparatus according to an embodiment.

MODE OF THE DISCLOSURE

Figure 1:
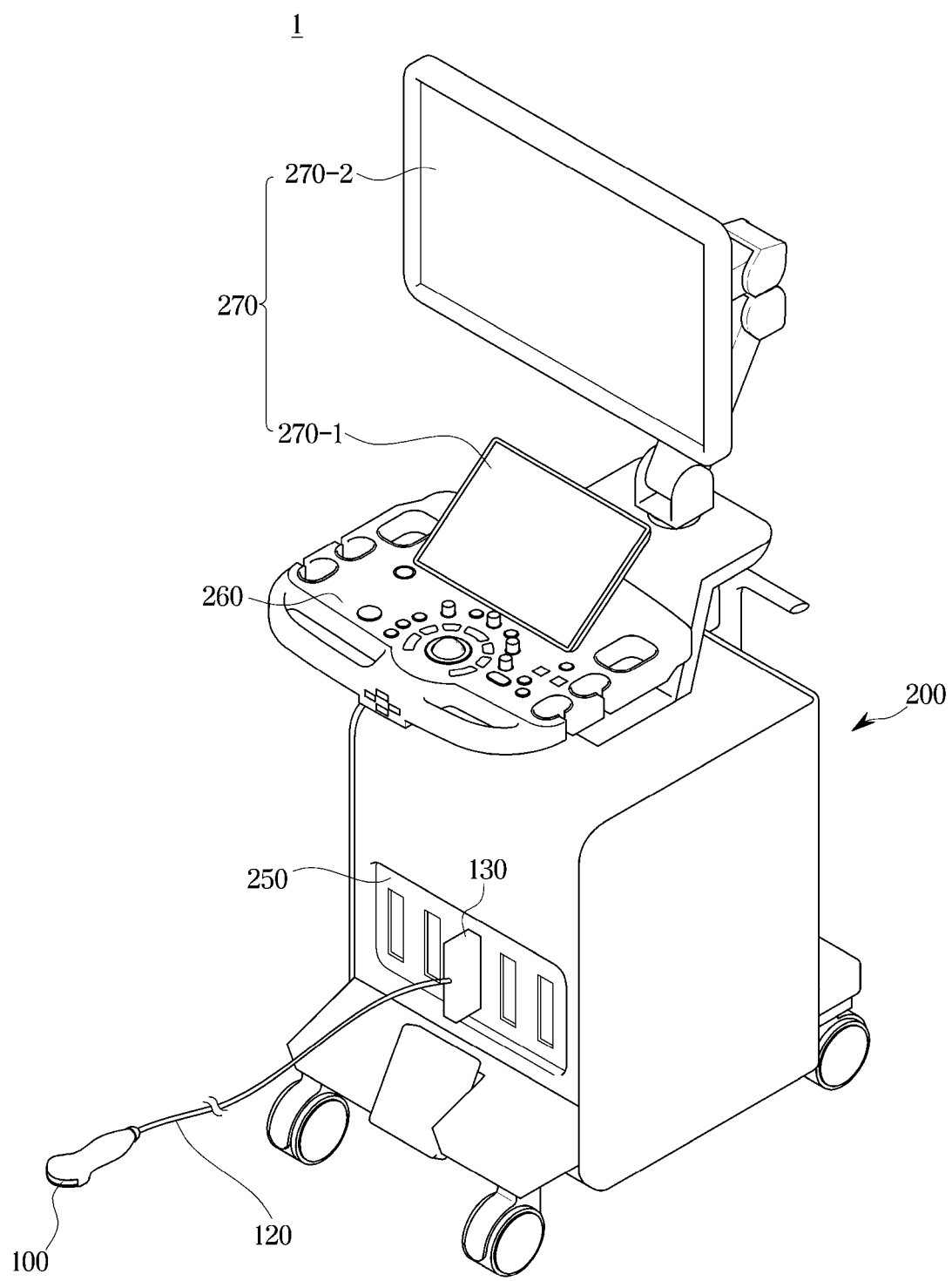
FIG. 1 is an external view of an ultrasonic imaging apparatus according to an embodiment.

Like numerals refer to like elements throughout the specification. Not all elements of embodiments of the present disclosure will be described, and description of what are commonly known in the art or what overlap each other in the embodiments will be omitted.

The terms as used throughout the specification, such as "~ part", "~ module", "~ member", "~ block", etc., may be implemented in software and/or hardware, and a plurality of "~ parts", "~ modules", "~ members", or "~ blocks" may be implemented in a single element, or a single "~ part", "~ module", "~ member", or "~ block" may include a plurality of elements.

It will be further understood that the term "connect" or its derivatives refer both to direct and indirect connection, and the indirect connection includes a connection over a wireless communication network.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless the context clearly indicates otherwise.

As used herein, the singular forms "a," "an" and "the" are intended to include the plural forms as well, unless the context clearly indicates otherwise.

Reference numerals used for method steps are just used for convenience of explanation, but not to limit an order of the steps. Thus, unless the context clearly dictates otherwise, the written order may be practiced otherwise.

A term 'object' may include a person or animal, or a part of a person or animal. For example, the object may include organs, such as liver, heart, uterus, brain, breast, abdomen, or blood vessels as well as a mass. Also, in the specification of the present disclosure, a term 'user' may be a doctor, a nurse, a clinical pathologist, a medical imaging expert, etc., and may be a technician who develops and repairs a medical device, but is not limited thereto.

Terms 'Ultrasound image' and 'object image' mean an image of an object obtained using ultrasound.

A term 'shear wave elastic image' refers to an image in which the shear wave elastic value for each area of an object obtained using ultrasound is displayed.

A term 'inefficiency region' refers to a region in which a self-signal exists without a push pulse, such as a blood vessel region in which blood flow exists and a region in which tissue movement occurs.

Hereinafter, an embodiment of an ultrasonic imaging apparatus and a method for controlling the same according to an aspect will be described in detail with reference to accompanying drawings.

FIG. 1 is an external view of an ultrasonic imaging apparatus according to an embodiment.

Referring to FIG. 1, the ultrasonic imaging apparatus 1 includes an ultrasonic probe 100 and a main body 200. The ultrasonic probe 100 may transmit an ultrasonic signal to an object to be diagnosed and receive an ultrasonic echo signal reflected from the object. The ultrasonic probe 100 receives the ultrasonic echo signal reflected from the object and converts it into an electrical signal (hereinafter, referred to as an ultrasonic signal).

The ultrasonic probe 100 is connected to the main body 200 of the ultrasonic imaging apparatus 1 through a cable 120, and may receive various signals necessary for controlling the ultrasonic probe 100 from the main body 200. Also, the ultrasonic probe 100 may transmit an analog signal or a digital signal corresponding to the ultrasonic echo signal to the main body 200.

Meanwhile, the ultrasonic probe 100 may be implemented as a wireless probe, and may transmit and receive signals through a network formed between the probe 100 and the main body 200.

The main body 200 may include a PSA board (Probe Select Assembly, 250), a control panel 260, and displays 270; 270-1 and 270-2. The PSA board 250 includes a port connected to the ultrasonic probe 100. The PSA board 250 may activate the ultrasonic probe 100 according to a command input of a user through the control panel 260 and the control of the controller 300. One end of the cable 120 includes a connector 130 connectable to a port of the PSA board 250.

The control panel 260 is a device that receives a command for operating the ultrasonic imaging apparatus 1 from the user. The control panel 260 may receive setting information regarding the probe 100 and may receive various control commands related to an operation of the main body 200.

The control panel 260 may include a keyboard. The keyboard may include a button, a switch, a knob, a touch pad, a trackball, and the like. Also, the control panel 260 may include a first display 270-1. The first display 270-1 may display a graphic user interface (GUI) for controlling an operation of the ultrasonic imaging apparatus 1. The first display 270-1 may display related information such as a menu for optimizing an ultrasound image or an auxiliary image.

The first display 270-1 may include a touch panel and may receive a touch input of the user for the graphic user interface. The first display 270-1 may display a graphic user interface having the same shape as a button included in the keyboard. The user may input a command for controlling the ultrasonic imaging apparatus 1 through a touch input to the first display 270-1.

The second display 270-2 may display an ultrasound image. The ultrasound image may be a 2D ultrasound image or a 3D stereoscopic ultrasound image, and various ultrasound images may be displayed according to an operation mode of the ultrasonic imaging apparatus 1. In addition, the second display 270-2 may display a menu necessary for ultrasound diagnosis, guide information, information about an operating state of the probe 100, and the like.

The second display 270-2 may display a shear wave elastic image by overlapping or matching the reference ultrasound image.

The second display 270-2 may also include a touch panel and receive a user's touch input for the graphic user interface. The user may input a command for controlling the ultrasonic imaging apparatus 1 through a touch input to the second display 270-2.

The display 270 may be implemented with various display devices, such as a liquid crystal display (LCD), a light emitting diode (LED), a plasma display panel (PDP), and an organic light emitting diode (OLED).

Figure 2:
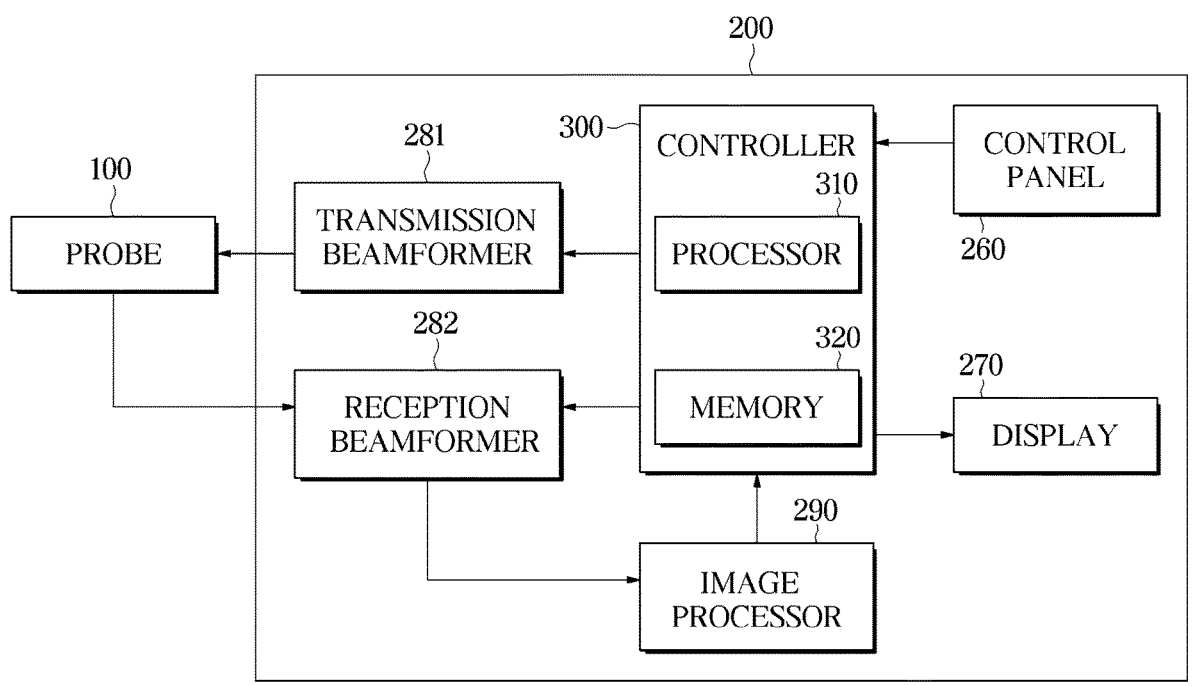
FIG. 2 is a block diagram of an ultrasonic imaging apparatus according to an embodiment.

FIG. 2 is a block diagram of an ultrasonic imaging apparatus according to an embodiment.

Referring to FIG. 2, the ultrasonic probe 100 may be a linear array probe, a curved array probe, a phased array probe, or a volume probe. The ultrasonic probe 100 is not limited thereto, and may include various probes such as an endocavity probe, a convex probe, a matrix probe, and/or a 3D probe.

The main body 200 of the ultrasonic imaging apparatus 1 may further include beamformers 281 and 282, an image processor 290, and a controller 300.

The beamformer may be divided into a transmission beamformer 281 and a reception beamformer 282. In obtaining an image using an ultrasound signal, a beamforming technology is applied to increase the resolution of the image. The transmission beamformer 281 may apply a transmit pulse to the ultrasonic probe 100. The transmission beamformer 281 may apply an appropriate time delay so that ultrasound signals to be transmitted by a plurality of transducer elements are simultaneously focused on one focal point, and may generate a transmission beam. The transducer array 110 may irradiate a transmission beam to a target portion within the object.

For convenience of description, such a transmission beam may be referred to as an 'observation signal' so as to be contrasted with a push pulse to be described later.

Also, the transmission beamformer 281 may generate a push pulse transmitted along a push line. The push pulse is irradiated to a region of interest of the object to induce tissue displacement and may induce a shear wave. The tissue displacement is used to measure the shear wave elastic value, which will be described later. The push pulse may be a focused beam having a relatively high focusing velocity.

The observation signal irradiated to the object may be reflected from the object and incident on the transducer array 110 of the ultrasonic probe 100 again. The reflected ultrasound signal may be defined as an ultrasound echo signal.

The reception beamformer 282 analog/digitizes the ultrasound echo signal received from the ultrasonic probe 100 and performs reception beamforming. The reception beamformer 282 may apply a time delay to the ultrasound echo signals that are reflected from the focal point and return to the transducer element, and may be summed at the same time.

Meanwhile, the beamformers 281 and 282 may be provided in the ultrasonic probe 100. For example, when the ultrasonic probe 100 is a wireless probe, the ultrasonic probe 100 may include beamformers 281 and 282.

The image processor 290 filters a noise component from the received beam to improve the quality of the ultrasound image, performs envelope detection processing for detecting the strength of the received signal, and generates digital ultrasound image data.

The image processor 290 may perform scan conversion for converting a scan line of the digital ultrasound image data so that the digital ultrasound image data may be displayed on the display 270. Also, the image processor 290 may perform image processing on the ultrasound echo signal to generate an A-mode image, a B-mode image, a D-mode image, an E-mode image, an M-mode image, a Doppler image, and/or a 3D ultrasound image. The image processor 290 performs RGB processing on ultrasound image data and transmits the ultrasound image data to the display 270 so that the ultrasound image may be displayed through the display 270.

Also, the image processor 290 may perform image processing to display various types of additional information on the ultrasound image.

Meanwhile, although the image processor 290 is illustrated separately from the controller 300 in FIG. 2, the controller 300 may include the image processor 290.

The display 270 may display an ultrasound image and various information processed by the ultrasonic imaging apparatus 1. The display 270 may display various graphic user interfaces for adjusting the generated ultrasound image.

The controller 300 may control the operation of the ultrasonic imaging apparatus 1 and the signal flow between internal components of the ultrasonic imaging apparatus 1. The controller 300 may include a processor 310 and a memory 320. The controller 300 may be implemented as a processing board in which the processor 310 and the memory 320 are installed on a circuit board. The processor 310 and the memory 320 may be connected through a bus. One or a plurality of processors 310 may be provided.

The controller 300 may be implemented with a plurality of logic gates, or may be implemented as a combination of a general-purpose micro-processor and a memory 320 in which a program executable in the microprocessor is stored.

The memory 320 refers to a storage medium for storing algorithms and data necessary for the operation of each component of the ultrasonic imaging apparatus 1. The memory 320 may include a high-speed random access memory, a magnetic disk, an SRAM, a DRAM, a ROM, and the like. Also, the memory 320 may be detachable from the ultrasonic imaging apparatus 1. The memory 320 may include, but is not limited to, a compact flash card (CF card), a secure digital card (SD card), a smart media card (SM card), a multimedia card (MMC), or a memory stick.

The controller 300 may be electrically connected to each of the PSA board 250, the control panel 260, the display 270, and the beamformers 281 and 282, and generate a control signal for controlling each component of the probe 100 and the main body 200.

Figure 4A:
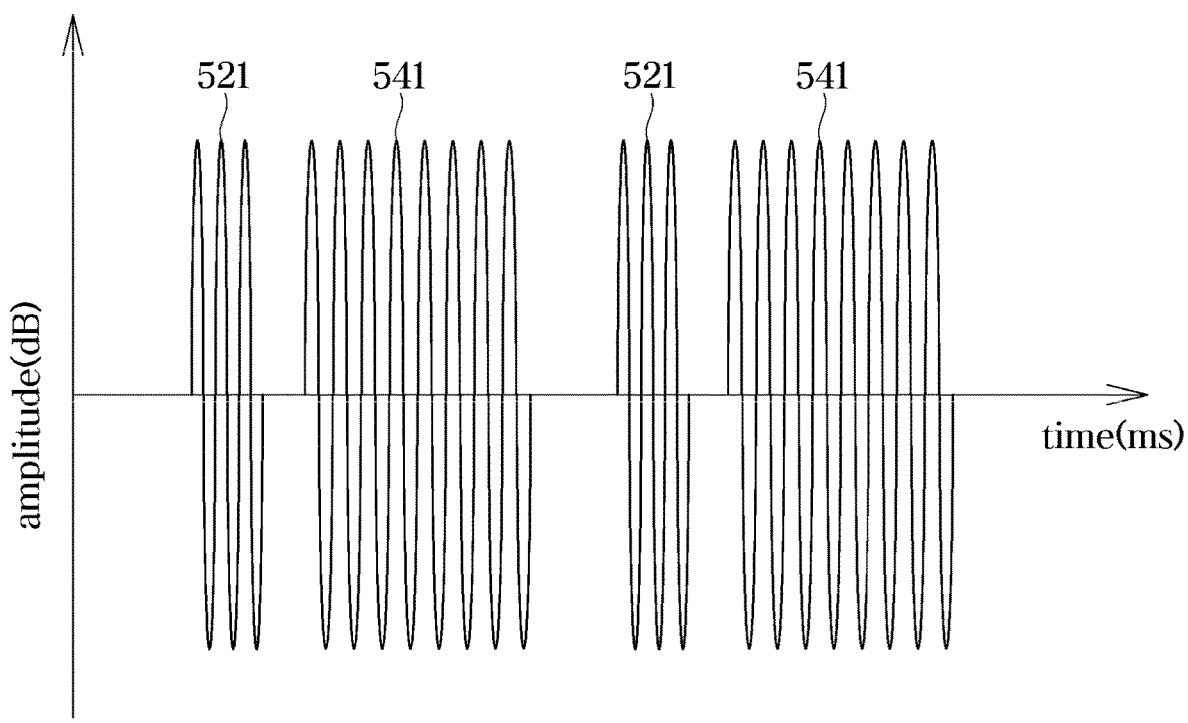
FIG. 4A is a view illustrating a push pulse and an observation signal irradiated by a conventional ultrasonic imaging apparatus.
Figure 4B:
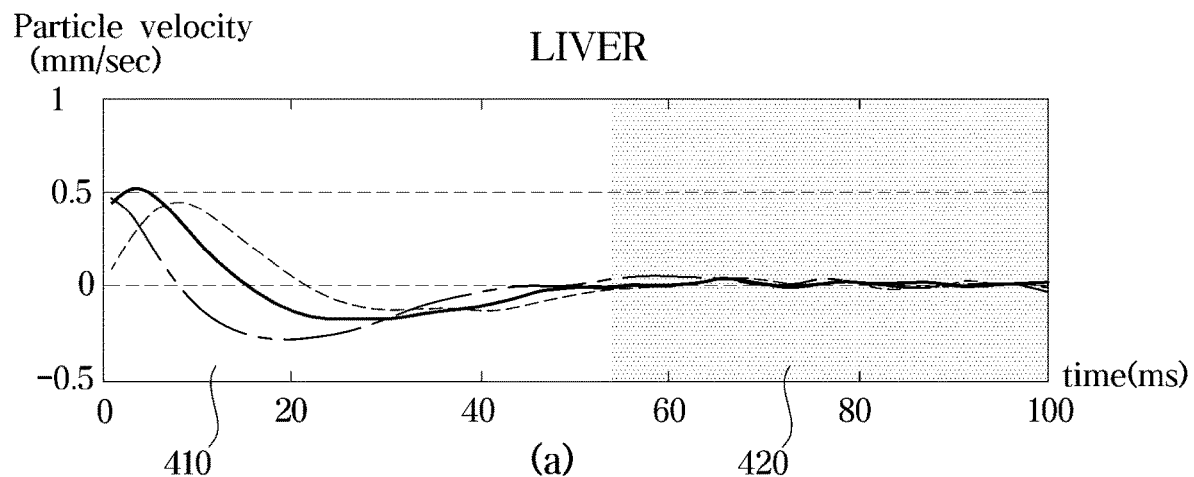
FIG. 4B is a view illustrating the shear wave velocity for each region obtained according to an observation signal irradiated by a conventional ultrasonic imaging apparatus over time.
Figure 4B:
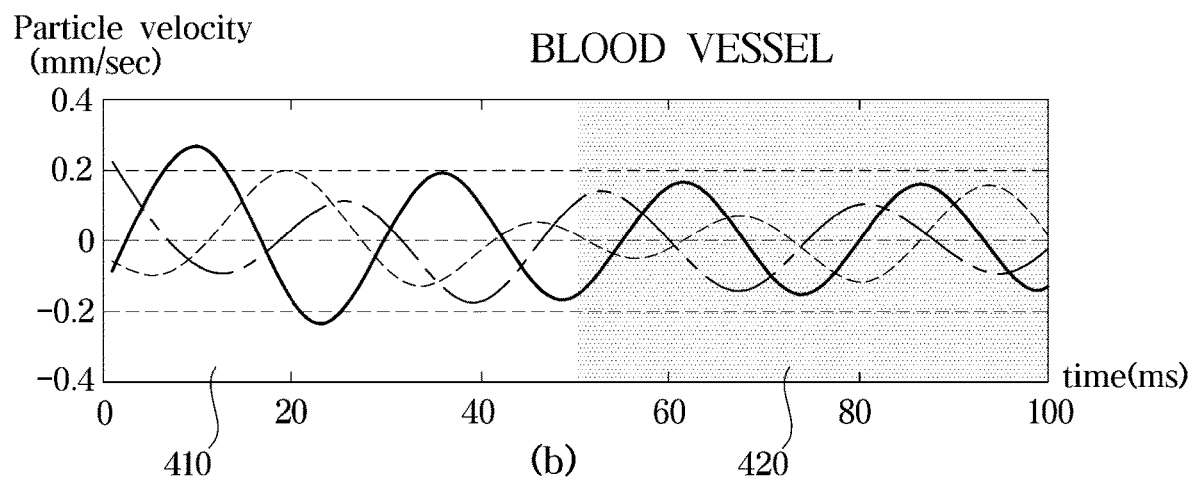
Figure 5A:
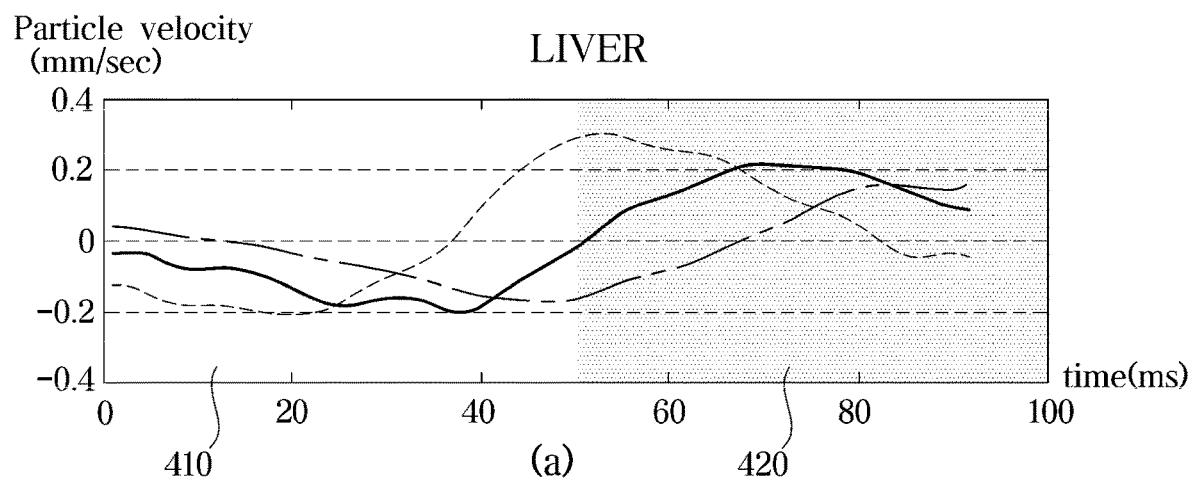
FIG. 5A is a view for explaining a case in which the shear wave velocity for each region exists in a second half.
Figure 5A:
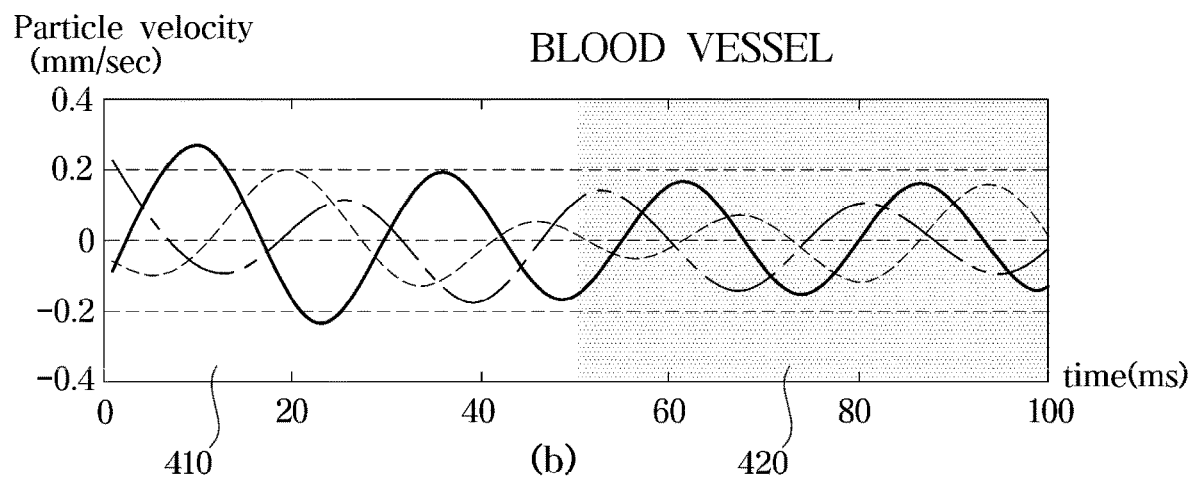

Hereinafter, a process in which a conventional ultrasonic imaging apparatus obtains a shear wave elastic image will be described with reference to FIGS. 3 to 5.

Figure 3:
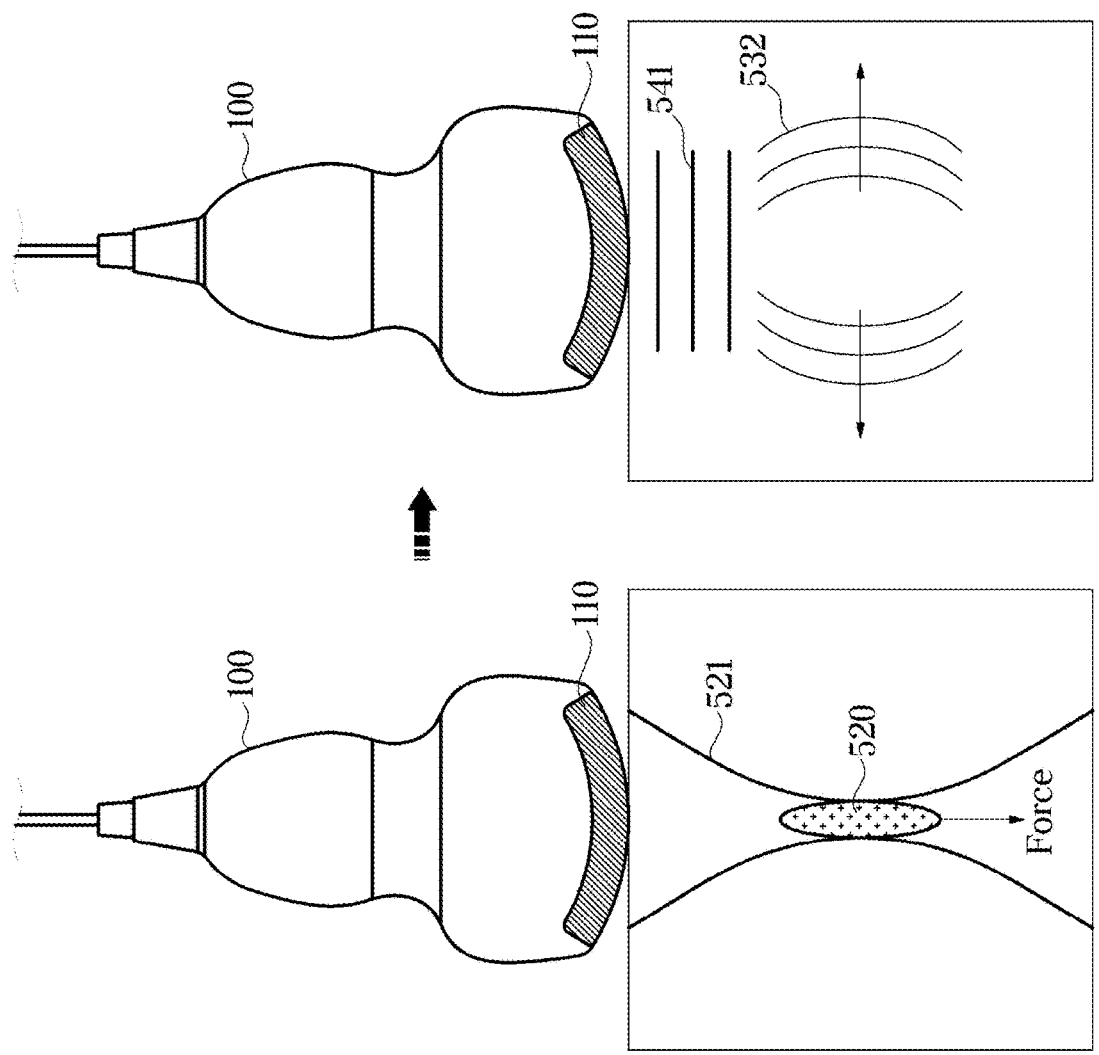
FIG. 3 is a view for explaining a process in which a conventional ultrasonic imaging apparatus obtains a shear wave elastic image.
Figure 5B:
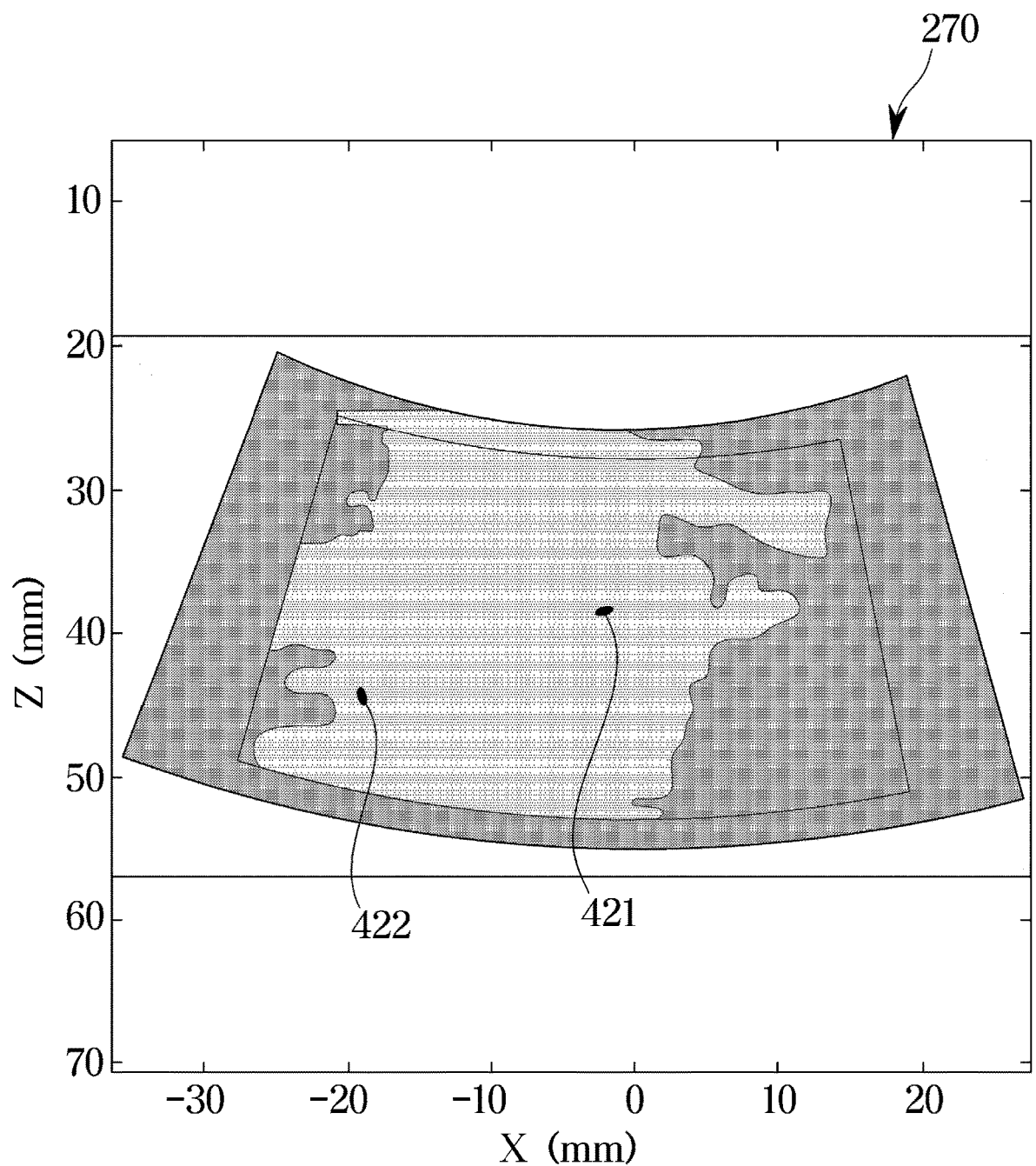
FIG. 5B is a view illustrating an ultrasound image obtained when the shear wave velocity for each region exists in a second half.

FIG. 3 is a view for explaining a process in which a conventional ultrasonic imaging apparatus obtains a shear wave elastic image. FIG. 4A is a view illustrating a push pulse and an observation signal irradiated by a conventional ultrasonic imaging apparatus. FIG. 4B is a view illustrating the shear wave velocity for each region obtained according to an observation signal irradiated by a conventional ultrasonic imaging apparatus over time. FIG. 5A is a view for explaining a case in which the shear wave velocity for each region exists in a second half. FIG. 5B is a view illustrating an ultrasound image obtained when the shear wave velocity for each region exists in a second half.

The content to be described later with reference to FIGS. 3 to 5 relates to a conventional ultrasonic imaging apparatus, but since the ultrasonic imaging apparatus according to an embodiment includes a configuration of the conventional ultrasonic imaging apparatus, for convenience of description, it may be described as the ultrasonic imaging apparatus 1 according to an embodiment.

Referring to FIG. 3, the ultrasonic probe 100 according to an embodiment may generate a shear wave 532 to the object by irradiating the push pulse 521 to the object along the push line under the control of the ultrasonic imaging apparatus 1. The push pulse 521 may be irradiated to the focal point 520 in the region of interest of the object to induce displacement of the object and generate the shear wave 532. The push pulse 521 is a focused beam having a relatively high focusing velocity and may have a narrow beam profile.

When the push pulse 521 is irradiated to the focal point 520 in the region of interest of the object, the shear wave 532 may be generated. That is, when a force is applied to the object of the focal point 520 in the depth direction by the push pulse, the object of the focal point 520 moves in the depth direction. The distance the object moves in the depth direction may be defined as displacement. Since the tissue of the object has a certain degree of elasticity and the adjacent tissues are organically connected, the movement of the object located at the focal point 520 also affects the adjacent tissues.

The displacement of the adjacent tissue is induced by the movement of the object located at the focal point 520. The shear wave 532 may propagate in a direction perpendicular to the depth direction. The shear wave 532 propagates in both directions from the focal point 520. The shear wave 532 changes its speed according to the vibratory properties of a medium. Therefore, the shear wave elastic value of the object may be obtained by estimating the velocity of the shear wave 532.

In addition, since the change in displacement or displacement, that is, the elastic value that occurs when a constant force is applied according to the characteristics of the medium, is different, so the shear wave elastic value of the object may be estimated based on the change or displacement of the displacement for each area of the object. In other words, the shear wave elastic value for each area of the object may be estimated based on the displacement data for each area of the object.

In order to estimate the velocity of the shear wave, that is, in order to obtain the shear wave elastic value of the object, the ultrasonic probe 100 according to an embodiment may irradiate the observation signal 541 to the object under the control of the ultrasonic imaging apparatus 1 after irradiating the push pulse 521. That is, the ultrasonic probe 100 may irradiate an observation signal 541 having a wide beam profile to the region of interest in which the shear wave 532 proceeds due to tissue displacement, and receive an ultrasonic echo signal in which the observation signal 541 is reflected from the region of interest. The ultrasonic imaging apparatus 1 may detect tissue displacement based on the echo signal of the observation signal 541.

For example, the controller 300 may obtain a shear wave elastic image at a high frame rate, and may detect tissue displacement by comparing successive shear wave elastic image frames.

However, when measuring the elastic value of the tissue using the shear wave 532, the accurate shear wave elastic value of the object may not be obtained due to blood vessels located in the region of interest of the object.

Specifically, when displacement data exists by itself due to blood flow without irradiation of the push pulse 521, such as blood vessels, or when there is a displacement change due to movement of the tissue without irradiation of the push pulse 521, it may be difficult to obtain an accurate shear wave elastic value of the tissue.

As described above, the elastic value for each area of the object may be determined based on the displacement data for each area of the object based on the displacement data for each area of the object from which the displacement, change of displacement, speed, etc. of the object by the shear wave 532 generated by the push pulse 521 may be estimated.

That is, determining the elastic value for each area of the object based on the displacement data may mean determining the elastic value for each area of the object based on the displacement, and determining the elastic value for each area of the object based on the displacement change per time, that is, the speed of the shear wave for each area of the object.

Hereinafter, with reference to FIGS. 4A to 4B, a process in which the ultrasonic imaging apparatus 1 according to the conventional art obtains an accurate shear wave elastic value of an object excluding a region in which its own signal such as a blood vessel exists will be described.

Referring to FIG. 4A, the order in which the conventional ultrasonic imaging apparatus irradiates the push pulse 521 and the observation signal 541 according to time may be confirmed. The ultrasonic imaging apparatus irradiates the push pulse 521 to the region of interest of the object, and then may irradiate the observation signal 541 to the object in order to observe the occurrence of displacement of the adjacent tissue.

That is, the push pulse 521 may be irradiated to the focal point 520 in the region of interest of the object, and the observation signal 541 may be irradiated to the region of interest of the object in order to observe the displacement data of the tissue resulting therefrom. In this case, for convenience of explanation, the observation signal 541 for observing the displacement data of the tissue due to the push pulse 521 may be defined as a 'first observation signal 541'.

In this case, the first observation signal 541 may include a plurality of ultrasound signals having a predetermined time interval. In this case, the predetermined time interval may be determined enough to observe the tissue displacement data by the push pulse 521.

That is, the first observation signal 541 is always irradiated for a predetermined time after the push pulse 521 is irradiated, so that the tissue displacement data by the push pulse 521 may be observed. In this case, the predetermined time may be determined as the time until the tissue displacement by the push pulse 521 disappears. As shown in FIG. 4A, in order to obtain a more accurate shear wave elastic value of an object, the ultrasonic imaging apparatus 1 may irradiate the push pulse and the first observation signal several times.

Although not shown in the figure, the controller 300 may determine the shear wave elastic value for each area of the object based on the displacement data for each area of the object obtained from the irradiated first observation signal 541, and obtain a shear wave elastic image based on the shear wave elastic value for each region of the object.

Referring to FIG. 4B, the velocity value of the particle in the object region corresponding to the tissue displacement data obtained from the irradiated first observation signal 541 may be confirmed.

Referring to part (a), which shows the particle velocity in the object region over time, it may be seen that the speed of particles in the object region is generated by the push pulse 521 in the first half 410 not long after the push pulse 521 is irradiated, but it may be confirmed that the particle velocity in the object region disappears in the second half 420 after a certain time has elapsed after the push pulse 521 is irradiated. That is, it may be confirmed that the shear wave 532 generated in the tissue disappears.

On the other hand, referring to part (b) showing the particle velocity in the blood vessel region over time, it may be seen that the particle velocity in the second half 420 does not disappear after a certain time has passed after the push pulse 521 is irradiated. That is, it may be confirmed that the particle velocity in the blood vessel region does not disappear.

Since the displacement of the blood vessel region occurs due to factors such as the movement of blood flow regardless of whether the push pulse 521 is irradiated or not, displacement data by the push pulse 521 may not be obtained, and thus accurate shear wave elastic value may not be obtained.

According to the fact that only the signal due to the change in displacement of the blood vessel region exists in the second half 420, the ultrasonic imaging apparatus according to the conventional art determines the region where displacement exists in the second half 420 as the blood vessel region, and displays the image so that the shear wave elastic value of the blood vessel region is not displayed.

Hereinafter, with reference to FIGS. 5A to 5B, a problem according to a method of determining a region in which displacement exists in the second half 420 as a blood vessel region will be described.

Referring to FIG. 5A, it may be confirmed that there is a change in displacement of the liver region in the second half 420 after a predetermined time has passed after the push pulse is irradiated.

When the first observation signal 541 is irradiated for a longer period of time, the displacement change in the liver region will disappear in the second half 420, but as described above, in order to obtain a shear wave elastic image at a high frame rate, it may be advantageous to shorten the irradiation time of the first observation signal 541 as much as possible.

The conventional ultrasonic imaging apparatus determines that the particle velocity is present in the second half 420 despite the liver region as a blood vessel region, and displays an image so that the shear wave elastic value of the region in which the particle velocity exists despite the liver region was not displayed.

That is, since particle velocities exist in the second half 420 of the blood vessel region and also in the second half 420 of the liver region, there is a problem that such a difference in particle velocities may not be distinguished.

Referring to FIG. 5B, a shear wave elastic image obtained by a conventional ultrasonic imaging apparatus may be confirmed. Looking at the shear wave elastic image obtained according to the conventional ultrasonic imaging apparatus, there is a portion 421 in which the elastic value is not displayed due to the presence of particle velocity in the latter part 420 as a blood vessel region, whereas although it is the liver region, there may be a portion 422 in which an elastic value is not displayed because particle velocity is present in the second half 420.

Due to these problems, the conventional ultrasonic imaging apparatus may not provide an accurate shear wave elastic image to the user and may reduce reliability of the user of the ultrasonic imaging apparatus.

Hereinafter, an ultrasonic imaging apparatus 1 according to an embodiment that may solve the above-described problems will be described with reference to FIGS. 6 to 8.

Figure 6A:
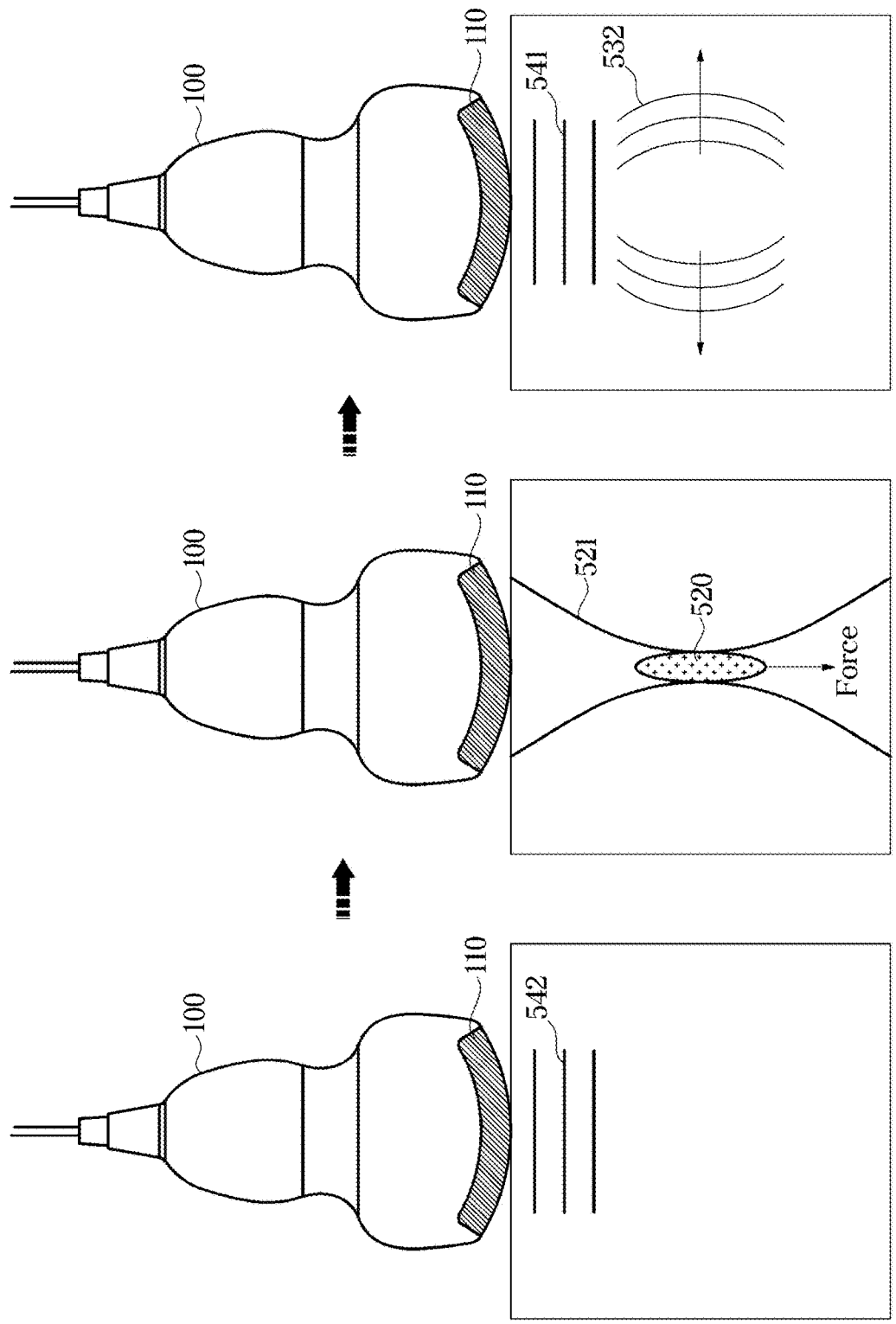
FIG. 6A is a view for explaining an ultrasonic irradiation process of an ultrasonic imaging apparatus according to an embodiment.
Figure 6B:
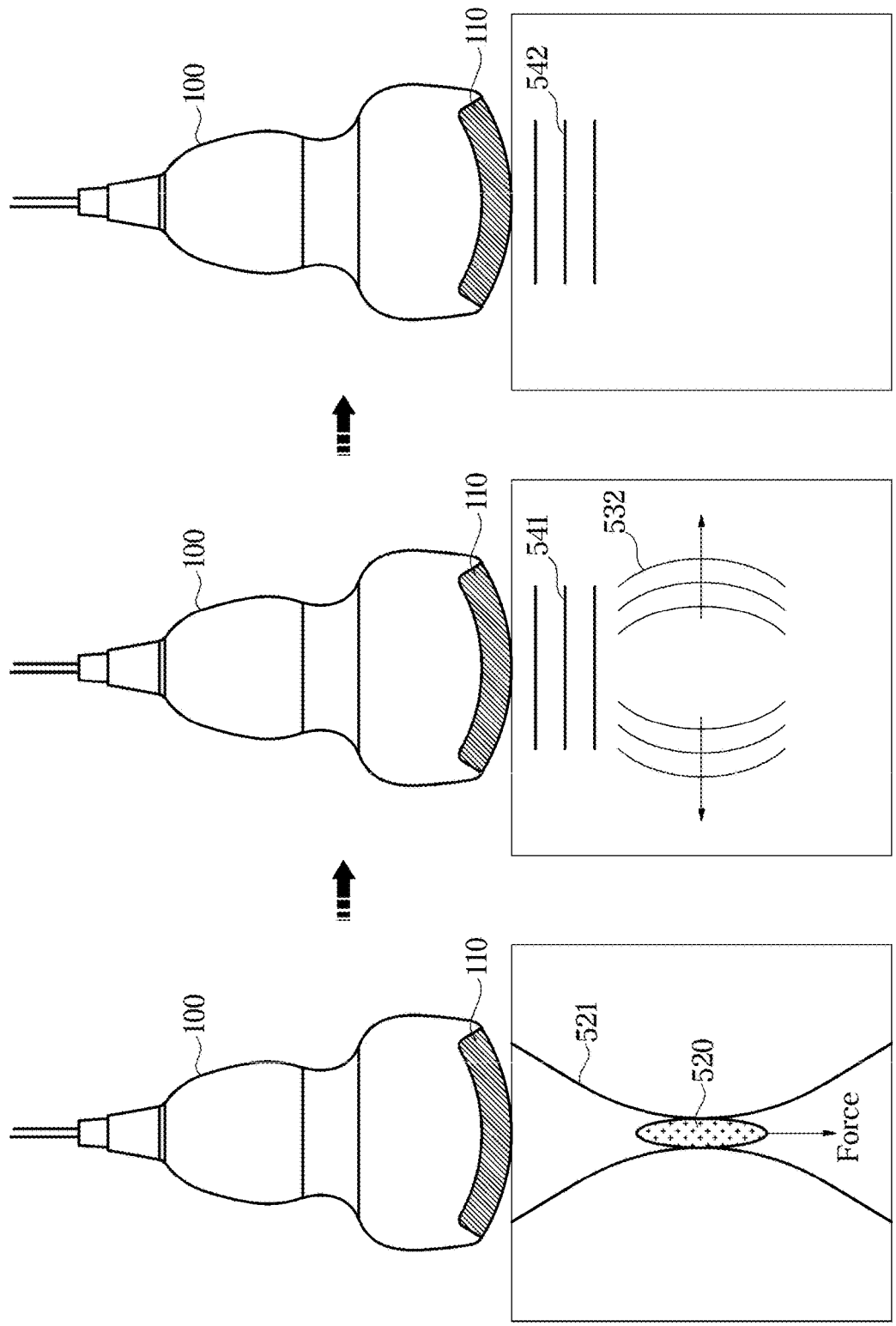
FIG. 6B is a view for explaining an ultrasonic irradiation process of an ultrasonic imaging apparatus according to another embodiment.

FIG. 6A is a view for explaining an ultrasonic irradiation process of an ultrasonic imaging apparatus according to an embodiment. FIG. 6B is a view for explaining an ultrasonic irradiation process of an ultrasonic imaging apparatus according to another embodiment.

Figure 7A:
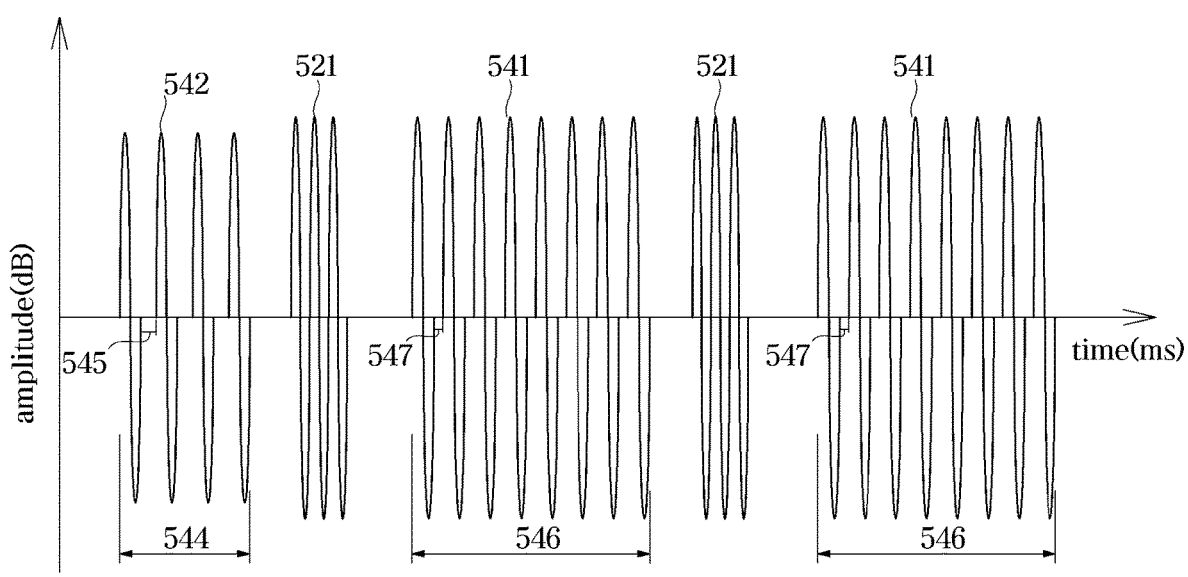
FIG. 7A is a view illustrating a push pulse, a first observation signal, and a second observation signal radiated by the ultrasonic imaging apparatus according to an embodiment.
Figure 7B:
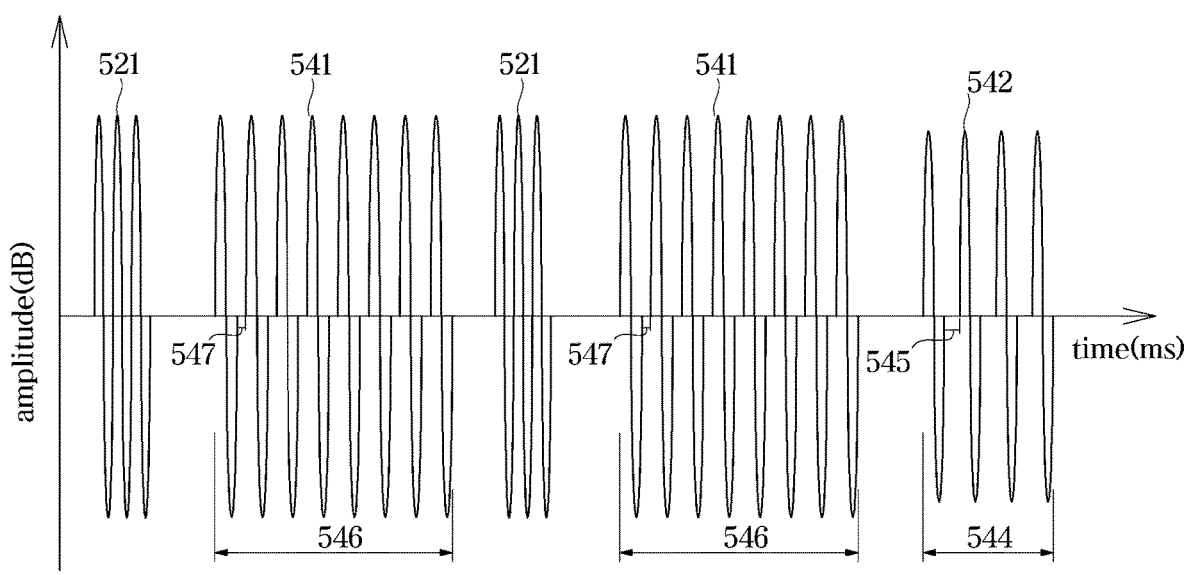
FIG. 7B is a view illustrating a push pulse, a first observation signal, and a second observation signal that are irradiated by the ultrasonic imaging apparatus according to another embodiment.

FIG. 7A is a view illustrating a push pulse, a first observation signal, and a second observation signal radiated by the ultrasonic imaging apparatus according to an embodiment. FIG. 7B is a view illustrating a push pulse, a first observation signal, and a second observation signal that are irradiated by the ultrasonic imaging apparatus according to another embodiment.

Figure 8:
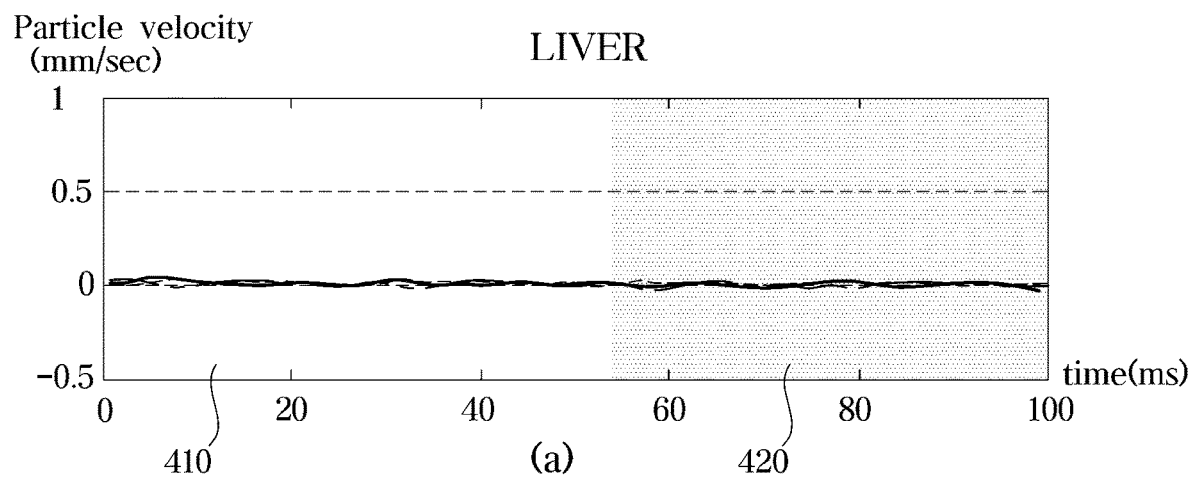
FIG. 8 is a view illustrating the shear wave velocity for each region obtained by irradiating the second observation signal over time.
Figure 8:
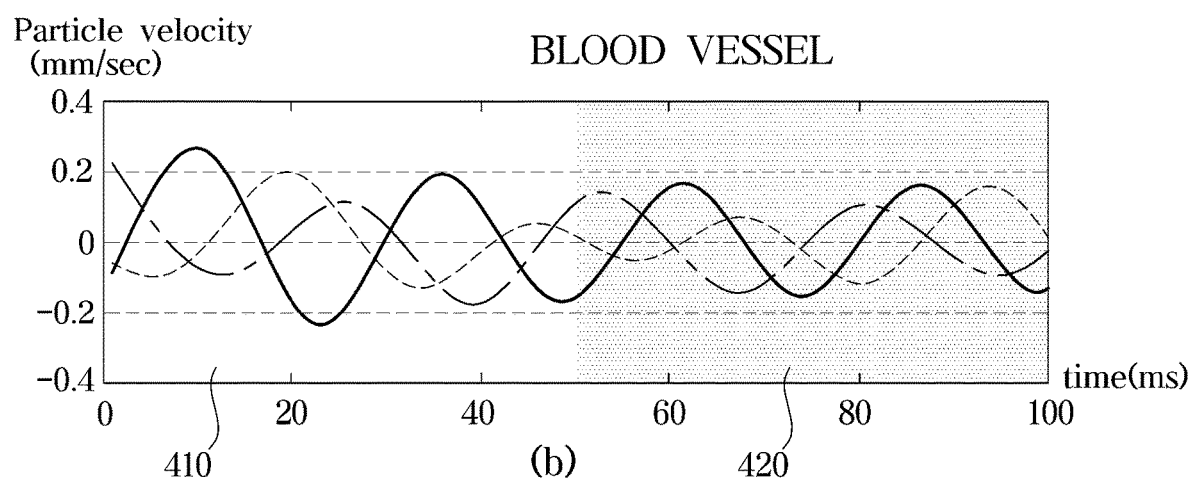

FIG. 8 is a view illustrating the shear wave velocity for each region obtained by irradiating the second observation signal over time.

Referring to FIG. 6A, the ultrasonic probe 100 according to an exemplary embodiment may irradiate the second observation signal 542 before the push pulse 521 is irradiated. That is, by using the second observation signal 542, displacement data for each region of the object in a state in which the shear wave 532 does not occur in the tissue may be obtained.

In this case, the controller 300 may determine the inefficiency region of the object based on the displacement data for each region of the object obtained from the irradiated second observation signal 542.

Referring to FIG. 8, it may be confirmed that the particle velocity in the liver region obtained from the irradiated second observation signal 542 is very small, and it may be confirmed that the particle velocity in the blood vessel region obtained from the irradiated second observation signal 542 exists.

The blood vessel region is a region included in the inefficiency region, and the inefficiency region may include at least one of a blood vessel region in which blood flow exists and a region in which tissue movement occurs.

That is, the inefficiency region may mean a region in which displacement changes even without the push pulse 52.

Accordingly, the controller 300, based on the displacement data for each area of the object obtained from the irradiated second observation signal 542, may determine a region in which a displacement value or a shear wave velocity value is greater than or equal to a predetermined value among regions of the object, and determine the determined region as an inefficiency region.

Referring back to FIG. 6A, as described with reference to FIG. 3, the ultrasonic probe 100 according to an embodiment may irradiate the push pulse 521 after the second observation signal 542 is irradiated, and obtain displacement data for each area of the object by irradiating the first observation signal 541 after the push pulse 521 is irradiated.

The controller 300 may generate a shear wave elastic image based on the determined inefficiency region and the displacement data for each region of the object obtained from the irradiated first observation signal 541, which will be described later with reference to FIGS. 9 to 10.

Referring to FIG. 6B, the ultrasonic probe 100 according to an embodiment may irradiate a first observation signal 541 after irradiating a push pulse 521 to obtain tissue displacement by the shear wave 532, and irradiate the second observation signal 542 after the first observation signal 541 is irradiated. After the push pulse 521 is irradiated and the first observation signal 541 is irradiated, the shear wave 532 caused by the push pulse 521 may disappear. Accordingly, by using the second observation signal 542, displacement data for each area of the object in a state in which the shear wave 532 is not generated by the push pulse 521 may be obtained.

In this case, the controller 300 may determine the inefficiency region based on the displacement data for each region of the object obtained from the irradiated second observation signal 542.

Specifically, the controller 300, based on the displacement data for each area of the object obtained from the irradiated second observation signal 542, may determine a region in which the displacement value or shear wave velocity value is greater than or equal to a predetermined value among regions of the object, and determine the determined region as an inefficiency region.

Referring to FIG. 8, it may be confirmed that the particle velocity in the liver region obtained from the irradiated second observation signal 542 is very small, and it may be confirmed that the particle velocity in the blood vessel region obtained from the irradiated second observation signal exists.

Referring to FIG. 7A, as shown in FIG. 6A, the ultrasonic probe 100 according to an embodiment may irradiate the second observation signal 542 before the push pulse 521 is irradiated. The second observation signal 542 may be irradiated to obtain displacement data for each area of the object without the influence of the push pulse 521, and then the push pulse 521 may be irradiated to generate the shear wave 532 in the object, and the first observation signal 541 may be irradiated to obtain displacement data for each area of the object generated by the generated shear wave 532.

Referring to FIG. 7B, as shown in FIG. 6B, the ultrasonic probe 100 according to an embodiment may generate the shear wave 532 on the object by irradiating a push pulse 521, and irradiate the first observation signal 541 to obtain displacement data for each region of the object generated by the generated shear wave 532. After irradiating the first observation signal 541, the second observation signal 542 may be irradiated to obtain displacement data for each area of the object that is not affected by the push pulse 521.

FIGS. 7A to 7B, the first observation signal 541 and the second observation signal 542 may include a plurality of ultrasound signals having predetermined time intervals.

In general, since the frequency range of blood vessels is about 500 Hz or less, in order to observe a signal of 500 Hz or less, the sampling frequency must be 2 kHz or more. Therefore, the signal for observing the displacement data of the blood vessel can be irradiated with a time interval of up to 500 microsecond. That is, it may be less than or equal to 500 microsecond.

In addition, in order to obtain the displacement data of the blood vessel, ½ cycle of the blood vessel needs to be observed, so the signal for observing the displacement data of the blood vessel may be irradiated for a time of at least 10 millisecond. That is, it may be irradiated for a time of 10 millisecond or more.

On the other hand, in general, in order to observe the displacement data for each area of the object by the push pulse 521, the sampling frequency must be 2 kHz or less, and the signal for observing the displacement data for each area of the object may be irradiated at a time interval shorter than a maximum of 500 microsecond. For example, it may be irradiated at an interval of at least 200 microsecond or less.

In addition, in order to obtain displacement data for each area of the object by the push pulse 521, since it is necessary to observe the displacement data for each area of the object until the displacement or displacement data by the push pulse 521 disappears, or until the shear wave generated by the push pulse 521 is transmitted to the tip of the tissue and the displacement data of the tip of the tissue may be obtained, a signal for obtaining displacement data for each area of the object by the push pulse 521 may be irradiated for a time longer than 10 millisecond. For example, it may be irradiated for at least 50 millisecond or longer.

Accordingly, the time interval 545 of each of the plurality of ultrasound signals included in the second observation signal 542 may be longer than or equal to the time interval 547 of each of the plurality of ultrasound signals included in the first observation signal 541, and the time 544 for which the second observation signal 542 is irradiated may be shorter than or equal to the time 546 for which the first observation signal 541 is irradiated.

Also, the second observation signal 542 may be irradiated for a time 544 of 10 millisecond or more, and a time interval 545 of each of the plurality of ultrasound signals included in the second observation signal 542 may be 500 microsecond or less.

Hereinafter, a process of generating a shear wave elastic image by the controller of the ultrasonic imaging apparatus 1 according to an embodiment and displaying it on the display 270 will be described with reference to FIGS. 9 to 10.

Figure 9:
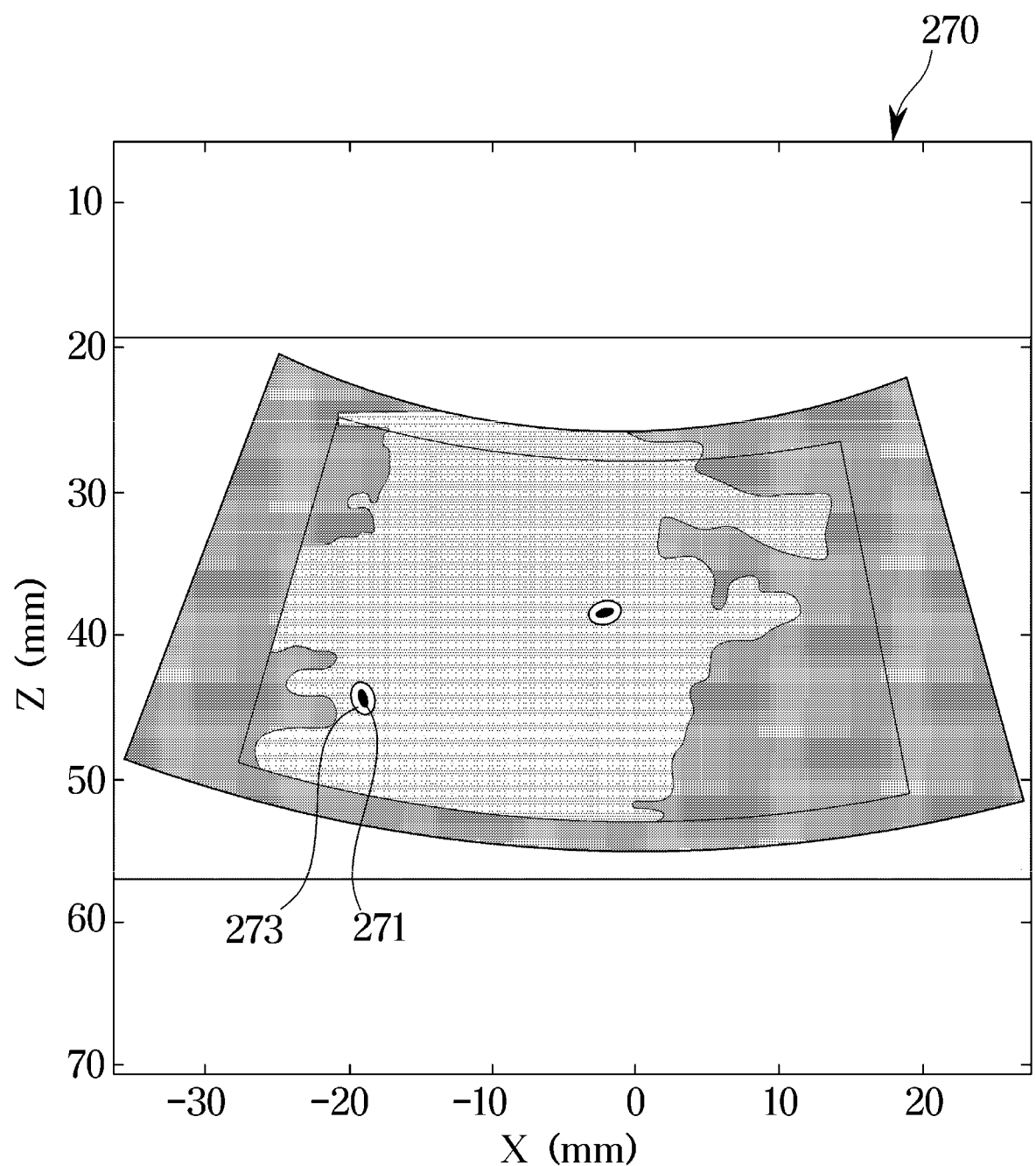
FIG. 9 is a view illustrating a display on which a shear wave elastic image is displayed, according to an exemplary embodiment.

FIG. 9 is a view illustrating a display on which a shear wave elastic image is displayed, according to an exemplary embodiment. FIG. 10 is a view illustrating a display unit on which a shear wave elastic image is displayed according to another exemplary embodiment.

As described above, the controller 300 according to an embodiment may determine the inefficiency region based on the displacement data for each region of the object obtained from the second observation signal 542 irradiated by the ultrasonic probe 10.

In addition, the controller 300 according to an embodiment may generate a shear wave elastic image based on the determined inefficiency region and the displacement data for each region of the object obtained from the first observation signal 541 irradiated by the ultrasonic probe 100, and display the generated shear wave elastic image on the display. Specifically, the controller 300 may determine the shear wave elastic value for each area of the object based on the displacement data for each area of the object obtained from the irradiated first observation signal 541, and generate the shear wave elastic image based on the determined shear wave elastic value for each region.

Referring to FIG. 9, the controller 300 according to an embodiment may determine the shear wave elastic value for each region of the object based on the displacement data for each region of the object obtained from the irradiated first observation signal 541, generate the shear wave elastic image based on the determined shear wave elastic value for each region, and generate a shear wave elastic image so that the determined shear wave elastic value of the inefficiency region 271 is not displayed.

Also, the controller 300 may control the display 270 to display a shear wave elastic image in which the shear wave elastic value of the determined inefficiency region 271 is not displayed.

When the ultrasound image is generated in B-mode, the inefficiency region 271 such as blood vessels is displayed in black on the display 270, so when the shear wave elastic value of the inefficiency region 271 marked in black is not displayed, the user can check only the area marked in black, so that it may be determined as the inefficiency region 271.

Also, the controller 300 according to an embodiment may control the display 270 to display the determined inefficiency region 271. For example, the controller 300 may control the display 270 to display a border 273 indicating the inefficiency region 271 with respect to the inefficiency region 271, but is not limited thereto.

Figure 10:
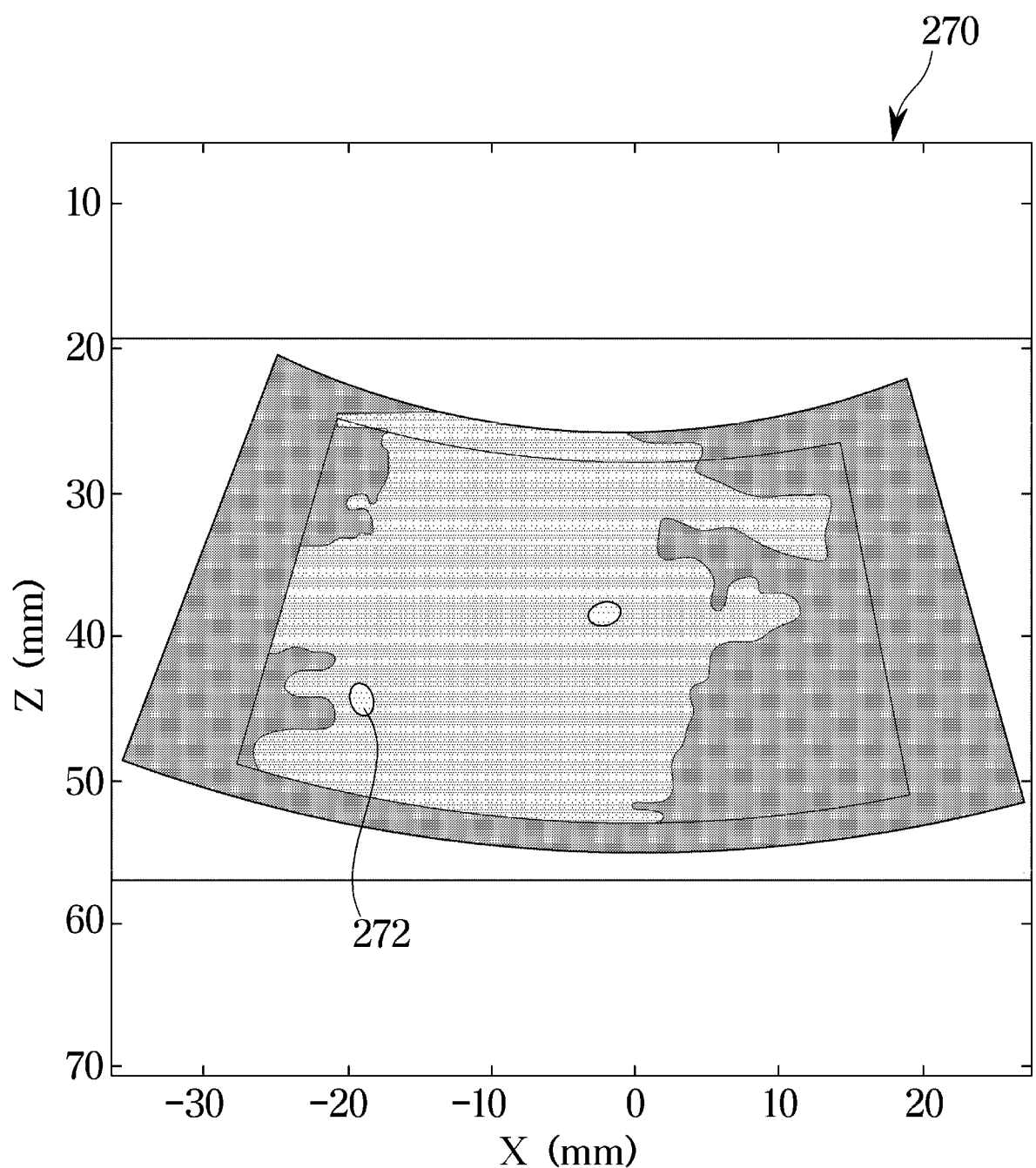
FIG. 10 is a view illustrating a display unit on which a shear wave elastic image is displayed according to another exemplary embodiment.

Referring to FIG. 10, the controller 300 according to an embodiment determines the shear wave elastic value for each region of the object based on the displacement data for each region of the object obtained from the irradiated first observation signal 541, generate the shear wave elastic image based on the determined shear wave elastic value for each region, and generate a shear wave elastic image by changing a reliability measurement index (RMI) of the determined shear wave elastic value of the inefficiency region 272.

In addition, the controller 300 may control the display 270 to display a shear wave elastic image to which a changed reliability measurement index (RMI) is applied as shown in FIG. 10, although not shown in the drawing, the display 270 may be controlled to display the changed reliability measurement index (RMI).

For example, the reliability measurement index of the shear wave elastic value of the inefficiency region 272 may be changed to 0, which means that the shear wave elastic value of the inefficiency region 272 is not displayed as described above in FIG. 9.

Also, for example, as shown in FIG. 10, the controller 300 may display the shear wave elastic value by changing the reliability measurement index of the shear wave elastic value of the inefficiency region 272 to a low value to obtain a smooth shear wave elastic image.

Hereinafter, a method of controlling the ultrasonic imaging apparatus 1 according to an embodiment will be described with reference to FIG. 11. FIG. 11 is a control flowchart of an ultrasonic imaging apparatus according to an embodiment.

The ultrasonic probe 100 according to an embodiment may irradiate a push pulse for generating a shear wave to the object to the object (1000). As described above, the push pulse may be irradiated to the focal point 520 in the region of interest of the object to induce displacement of the object and to induce a shear wave.

When the push pulse is irradiated to the focal point within the region of interest of the object, a shear wave may be generated. That is, when a force is applied to the object at the focal point in the depth direction by the push pulse, the object at the focal point moves in the depth direction. The distance the object moves in the depth direction may be defined as displacement. Since the tissue of the object has a certain elasticity and the adjacent tissues are organically connected, the movement of the object located at the focal point also affects the adjacent tissues.

In addition, the ultrasonic probe 100 according to an embodiment may irradiate the first observation signal after the push pulse is irradiated in order to obtain displacement data for each region of the object by the generated shear wave (1100).

Also, the ultrasonic probe 100 according to an embodiment may radiate the second observation signal after the first observation signal is irradiated (1200), and irradiate the second observation signal before (between 1000 and the start) the push pulse is irradiated to the object regardless of the order of the flowchart. That is, the step 1200 of irradiating the second observation signal may be performed after the first observation signal is irradiated (after 1100) or before the push pulse is irradiated to the object (between 1000 and the start).

Thereafter, the controller 300 according to an embodiment may determine the inefficiency region of the object based on the displacement data for each region of the object obtained from the irradiated second observation signal (1300).

At this time, determining of the inefficiency region based on the displacement data for each region of the object obtained from the irradiated second observation signal, may include determining a region of the object region in which a displacement value or a shear wave velocity value is greater than or equal to a predetermined value, based on the displacement data for each region of the object obtained from the second observation signal irradiated, and determining the determined region as an inefficiency region.

As described above, the inefficiency region may include at least one of a blood vessel region in which blood flow exists and a region in which tissue movement occurs.

Thereafter, the controller 300 according to an embodiment may generate a shear wave elastic image based on the displacement data for each region of the object obtained from the irradiated first observation signal and the determined inefficiency region (1400).

At this time, generating of the shear wave elastic image may include determining the shear wave elastic value for each area of the object based on the displacement data for each area of the object obtained from the irradiated first observation signal, generating the shear wave elastic image based on the determined shear wave elastic value for each region, and generating a shear wave elastic image so that the shear wave elastic value of the determined inefficiency region is not displayed.

In addition, generating of the shear wave elastic image may include determining the shear wave elastic value for each area of the object based on the displacement data for each area of the object obtained from the irradiated first observation signal, generating a shear wave elastic image based on the determined shear wave elastic value for each region, and generating a shear wave elastic image by changing a reliability measurement index (RMI) of the shear wave elastic value of the determined inefficiency region.

Thereafter, the display 270 according to an embodiment may display the generated shear wave elastic image (1500). At this time, a shear wave elastic image in which the shear wave elastic value of the determined inefficiency region is not displayed may be displayed.

In addition, a shear wave elastic image to which a changed reliability measurement index (RMI) is applied may be displayed, and a changed reliability measurement index (RMI) may be displayed.

In addition, the determined inefficiency region may be displayed by displaying a border indicating that the inefficiency region is the determined inefficiency region.

Meanwhile, the disclosed embodiments may be embodied in the form of a recording medium storing instructions executable by a computer. The instructions may be stored in the form of program code and, when executed by a processor, may generate a program module to perform the operations of the disclosed embodiments. The recording medium may be embodied as a computer-readable recording medium.

The computer-readable recording medium includes all kinds of recording media in which instructions which may be decoded by a computer are stored, for example, a Read Only Memory (ROM), a Random Access Memory (RAM), a magnetic tape, a magnetic disk, a flash memory, an optical data storage device, and the like.

Although exemplary embodiments of the present invention have been described for illustrative purposes, those skilled in the art will appreciate that various modifications, additions and substitutions are possible, without departing from the scope and spirit of the present invention. Therefore, exemplary embodiments of the present invention have not been described for limiting purposes.

The invention claimed is:

1. An ultrasonic imaging apparatus, comprising:
an ultrasonic probe configured to irradiate a push pulse to generate a shear wave to an object, irradiate a first observation signal for observing a displacement of the object caused by the push pulse to the object after the push pulse is irradiated, and irradiate a second observation signal for observing a displacement of a blood vessel that occurs regardless of the push pulse to the object before the push pulse is irradiated or after the first observation signal is irradiated;

a controller configured to determine an inefficiency region of the object containing blood flow based on displacement data obtained from the irradiated second observation signal that indicates the displacement of the blood vessel that occurs regardless of the push pulse, and generate a shear wave elastic image based on the determined inefficiency region and displacement data for each region of the object obtained from the irradiated first observation signal; and a display configured to display the generated shear wave elastic image, wherein the second observation signal is irradiated for a time more than 10 milliseconds for observing more than half cycle of the blood vessel and shorter than a time for which the first observation signal is irradiated, wherein the first observation signal and the second observation signal include a plurality of ultrasound signals having a predetermined time interval, wherein a time interval of each of the plurality of ultrasound signals included in the second observation signal is less than or equal to 500 microseconds for observing the displacement of the blood vessel, a time interval of each of the plurality of ultrasound signals included in the first observation signal is less than or equal to 200 microseconds for observing the displacement of the object caused by the push pulse, and the time interval of each of the plurality of ultrasound signals included in the second observation signal is longer than the time interval of each of the plurality of ultrasound signals included in the first observation signal, wherein the controller is configured to determine a region in which a displacement value or a shear wave velocity value is greater than or equal to a predetermined value among regions of the object based on the displacement data for each region of the object obtained from the irradiated second observation signal, and determine the determined region as the inefficiency region.

2. The ultrasonic imaging apparatus according to claim 1, wherein the inefficiency region further includes a region in which tissue movement occurs regardless of the push pulse.

3. The ultrasonic imaging apparatus according to claim 1, wherein the controller is configured to:
determine a shear wave elastic value for each region of the object based on the displacement data for each region of the object obtained from the irradiated first observation signal, and generate the shear wave elastic image of the object based on the determined shear wave elastic value for each region, wherein the shear wave elastic image is generated to prevent the shear wave elastic value of the determined inefficiency region from being displayed.

4. The ultrasonic imaging apparatus according to claim 3, wherein the controller is configured to control the display to display the shear wave elastic image in which the shear wave elastic value of the determined inefficiency region is prevented from being displayed.

5. The ultrasonic imaging apparatus according to claim 1, wherein the controller is configured to:
determine a shear wave elastic value for each region of the object based on the displacement data for each region of the object obtained from the irradiated first observation signal, and generate the shear wave elastic image of the object based on the determined shear wave elastic value for each region, wherein the shear wave elastic image is generated by changing a reliability measurement index (RMI) of the shear wave elastic value of the determined inefficiency region.

6. The ultrasonic imaging apparatus according to claim 5, wherein the controller is configured to control the display to display the shear wave elastic image to which the changed RMI is applied.

7. The ultrasonic imaging apparatus according to claim 5, wherein the controller is configured to control the display to display the RMI.

8. The ultrasonic imaging apparatus according to claim 1, wherein the controller is configured to control the display to display the determined inefficiency region.

9. A method for controlling an ultrasonic imaging apparatus, the method comprising:
irradiating a second observation signal to an object for observing a displacement of a blood vessel that occurs regardless of a push pulse;
irradiating the push pulse for generating a shear wave to the object after the second observation signal is irradiated to the object;
irradiating a first observation signal for observing a displacement of the object caused by the push pulse to the object after the push pulse is irradiated;
determining an inefficiency region of the object containing blood flow based on displacement data obtained from the irradiated second observation signal that indicates the displacement of the blood vessel that occurs regardless of the push pulse;
generating a shear wave elastic image based on displacement data for each region of the object obtained from the irradiated first observation signal and the determined inefficiency region; and
displaying the generated shear wave elastic image,
wherein the second observation signal is irradiated for a time more than 10 milliseconds for observing more than half cycle of the blood vessel and shorter than a time for which the first observation signal is irradiated,
wherein the first observation signal and the second observation signal include a plurality of ultrasound signals having a predetermined time interval,
wherein a time interval of each of the plurality of ultrasound signals included in the second observation signal is less than or equal to 500 microseconds for observing the displacement of the blood vessel, a time interval of each of the plurality of ultrasound signals included in the first observation signal is less than or equal to 200 microseconds for observing the displacement of the object caused by the push pulse, and the time interval of each of the plurality of ultrasound signals included in the second observation signal is longer than the time interval of each of the plurality of ultrasound signals included in the first observation signal,
wherein determining the inefficiency region of the object comprises:
determining a region in which a displacement value or a shear wave velocity value is greater than or equal to a predetermined value among regions of the object based on the displacement data for each region of the object obtained from the irradiated second observation signal, and
determining the determined region as the inefficiency region.

10. A method for controlling an ultrasonic imaging apparatus, the method comprising:
irradiating a push pulse to an object to generate a shear wave in the object; irradiating a first observation signal for observing a displacement of the object caused by the push pulse to the object after the push pulse is irradiated;

irradiating a second observation signal for observing a displacement of a blood vessel that occurs regardless of the push pulse to the object after the first observation signal is irradiated;

determining an inefficiency region of the object containing blood flow based on displacement data obtained from the irradiated second observation signal that indicates movement the displacement of the blood vessel that occurs regardless of the push pulse;

generating a shear wave elastic image based on displacement data for each region of the object obtained from the irradiated first observation signal and the determined inefficiency region; and displaying the generated shear wave elastic image, wherein the second observation signal is irradiated for a time more than 10 milliseconds for observing more than half cycle of the blood vessel and shorter than a time for which the first observation signal is irradiated, wherein the first observation signal and the second observation signal include a plurality of ultrasound signals having a predetermined time interval, wherein a time interval of each of the plurality of ultrasound signals included in the second observation signal is less than or equal to 500 microseconds for observing the displacement of the blood vessel, a time interval of each of the plurality of ultrasound signals included in the first observation signal is less than or equal to 200 microseconds for observing the displacement of the object caused by the push pulse, and the time interval of each of the plurality of ultrasound signals included in the second observation signal is longer than the time interval of each of the plurality of ultrasound signals included in the first observation signal, wherein determining the inefficiency region of the object comprises:

determining a region in which a displacement value or a shear wave velocity value is greater than or equal to a predetermined value among regions of the object based on the displacement data for each region of the object obtained from the irradiated second observation signal, and determining the determined region as the inefficiency region.

\* \* \* \* \*